(12) United States Patent
Wang et al.

(10) Patent No.: US 8,119,705 B2
(45) Date of Patent: Feb. 21, 2012

(54) METHOD OF FABRICATING POLYMER BLEND-BIOCERAMIC COMPOSITE IMPLANTABLE MEDICAL DEVICES

(75) Inventors: Yunbing Wang, Mountain View, CA (US); David C. Gale, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/911,637

(22) Filed: Oct. 25, 2010

(65) Prior Publication Data

US 2011/0057339 A1    Mar. 10, 2011

Related U.S. Application Data

(62) Division of application No. 11/529,996, filed on Sep. 29, 2006, now Pat. No. 7,842,737.

(51) Int. Cl.
  *A61F 2/04* (2006.01)
  *C08L 53/00* (2006.01)
  *C08F 6/24* (2006.01)
  *C08J 3/11* (2006.01)
  *C08G 63/08* (2006.01)

(52) U.S. Cl. ........... 523/113; 528/354; 528/480; 525/88

(58) Field of Classification Search .................. 523/113; 528/354, 480; 525/88
  See application file for complete search history.

(56) References Cited

U.S. PATENT DOCUMENTS

| 4,744,365 A | 5/1988 | Kaplan et al. |
| 6,165,486 A | 12/2000 | Marra et al. |
| 7,241,856 B2 | 7/2007 | Jin et al. |
| 2003/0065355 A1 | 4/2003 | Weber |
| 2003/0099683 A1 | 5/2003 | Grunze |
| 2004/0260386 A1 | 12/2004 | Shalaby |
| 2006/0171985 A1 | 8/2006 | Richard et al. |
| 2006/0264531 A1 | 11/2006 | Zhao |
| 2007/0207186 A1 | 9/2007 | Scanlon et al. |
| 2007/0231365 A1 | 10/2007 | Wang et al. |
| 2008/0063685 A1 | 3/2008 | Wang et al. |
| 2008/0147165 A1 | 6/2008 | Hossainy et al. |

FOREIGN PATENT DOCUMENTS

| EP | 1 462 124 | 9/2004 |
| EP | 1 600 178 | 11/2005 |
| WO | WO 98/46164 | 10/1998 |

OTHER PUBLICATIONS

International Search Report for PCT/US2007/020129 filed Sep. 17, 2007, mailed Mar. 5, 2008, 6 pgs.
International Search Report for PCT/US2007/088184, mailed Mar. 11, 2009, 7 pgs.
Broz et al., "Structure and mechanical properties of poly(D,L-lactic acid)/ poly(ε-caprolactone) blends", Biomaterials 24, pp. 4181-4190 (2003).
Kikuchi et al., "Development of guided bone regeneration membrane composed of β-tricalcium phosphate and poly (L-lactide-*co*-glycolide-*co*-ε-caprolactone) composites", Biomaterials 25, pp. 5979-5986 (2004).

*Primary Examiner* — Tae H Yoon
(74) *Attorney, Agent, or Firm* — Squire Sanders (US) LLP

(57) ABSTRACT

Methods and devices relating to polymer blend/bioceramic composite implantable medical devices are disclosed.

14 Claims, 7 Drawing Sheets

METHOD OF FABRICATING POLYMER BLEND-BIOCERAMIC COMPOSITE IMPLANTABLE MEDICAL DEVICES

CROSS REFERENCE TO RELATED APPLICATION

This application is a divisional application of U.S. patent application Ser. No. 11/529,996 which was filed on Sep. 29, 2006, now U.S. Pat. No. 7,842,737, which is incorporated by reference herein.

BACKGROUND OF THE INVENTION

1. Field of the Invention

This invention relates to implantable medical devices and methods of fabricating implantable medical devices.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Potential problems with polymeric stents is that they may have inadequate toughness and they may have a degradation rate that is slower than is desirable for certain treatments.

SUMMARY OF THE INVENTION

Certain embodiments of the present invention include a method for fabricating an implantable medical device comprising: forming a suspension solution including a fluid, a matrix polymer and bioceramic particles, wherein the polymer is dissolved in the fluid, and wherein the bioceramic particles are dispersed in the solution; allowing at least some of matrix polymer to precipitate upon combining the suspension solution with a second fluid, the second fluid being a poor solvent for the matrix polymer, wherein at least some of the bioceramic particles precipitate with the precipitated polymer to form a composite mixture; mixing the composite mixture with a modifier polymer and additional matrix polymer to form a second composite mixture, the bioceramic particles being dispersed within the second composite mixture by the mixing, wherein the modifier polymer has discrete phase segments, the discrete phase segments being immiscible with the matrix polymer, the modifier polymer further comprising anchor segments that are miscible with the matrix polymer; and fabricating a medical device from the second composite mixture.

Further embodiments of the present invention include a method for fabricating an implantable medical device comprising: forming a suspension solution including a fluid, a modifier polymer and bioceramic particles, wherein the polymer is dissolved in the fluid, and wherein the bioceramic particles are dispersed in the solution; allowing at least some of modifier polymer to precipitate upon combining the suspension solution with a second fluid, the second fluid being a poor solvent for the modifier polymer, wherein at least some of the bioceramic particles precipitate with the precipitated polymer to form a composite mixture; mixing the composite mixture with the modifier polymer and a matrix polymer to form a second composite mixture, the bioceramic particles being dispersed within the second composite mixture by the mixing, wherein the modifier polymer has discrete phase segments, the discrete phase segments being immiscible with the matrix polymer, the modifier polymer further comprising anchor segments that are miscible with the matrix polymer; and fabricating a medical device from the second composite mixture.

DETAILED DESCRIPTION OF THE INVENTION

Various embodiments of the present invention include an implantable medical device fabricated at least in part of a polymer blend/bioceramic composite including a polymer blend and bioceramic particles dispersed within the blend. The polymer blend can have a continuous polymer phase and a discrete polymer phase within the continuous polymer phase. The bioceramic particles can be dispersed within the continuous phase, the discrete polymer phase, or both.

As used herein, an "implantable medical device" includes, but is not limited to, self-expandable stents, balloon-expandable stents, stent-grafts, implantable cardiac pacemakers and defibrillators, leads and electrodes for the preceding, vascular grafts, grafts, artificial heart valves, and cerebrospinal fluid shunts.

An implantable medical device can be designed for the localized delivery of a therapeutic agent. A medicated implantable medical device may be constructed by coating the device or substrate with a coating material containing a therapeutic agent. The substrate of the device may also contain a therapeutic agent.

Figure 1A:
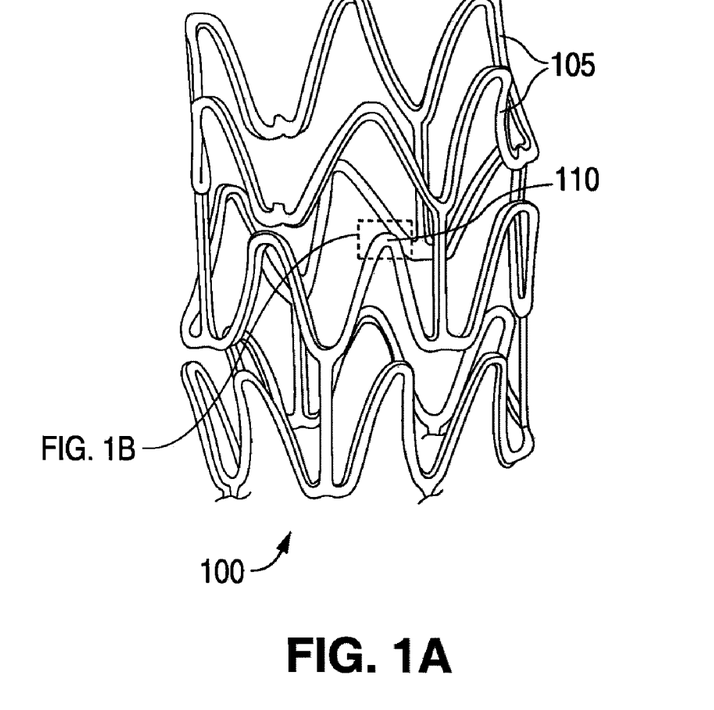
FIG. 1A depicts a three-dimensional view of a stent.

FIG. 1A depicts a three-dimensional view of a stent 100. In some embodiments, a stent may include a pattern or network of interconnecting structural elements 105. Stent 100 may be formed from a tube (not shown). The pattern of structural elements 110 can take on a variety of patterns. The structural pattern of the device can be of virtually any design. The embodiments disclosed herein are not limited to stents or to the stent pattern illustrated in FIG. 1A. The embodiments are easily applicable to other patterns and other devices. The variations in the structure of patterns are virtually unlimited. A stent such as stent 100 may be fabricated from a tube by forming a pattern with a technique such as laser cutting or chemical etching.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

Some polymers that may be suitable for implantable medical devices such as stents have potential shortcomings. For example, some biodegradable polymers have a degradation rate that is slower than desired for certain stent treatments. As a result, the degradation time of a stent made from such polymers can be longer than desired. For example, a stent made from poly(L-lactide) (PLLA) can have a degradation time of between about two and three years. In some treatment situations, a degradation time of less than a year may be desirable, for example, between four and eight months.

The degradation of a hydrolytically degradable polymer follows a sequence including water penetration into the polymer followed by hydrolysis of bonds in the polymer. Thus, the degradation of a polymer can be influenced by its affinity for water and the diffusion rate of water through the polymer. A hydrophobic polymer has a low affinity for water which results in a relatively low water penetration. In addition, the diffusion rate of water through crystalline regions of a polymer is lower than amorphous regions. Thus, as either the affinity of a polymer for water decreases or the crystallinity increases, water penetration and water content of a polymer decreases.

Another shortcoming of some polymers is that their toughness is lower than desired, in particular, for use in stent applications. For example, polymers such as PLLA tend to be brittle under physiological conditions or conditions within a human body. Specifically, such polymers can have a Tg above human body temperature which is approximately 37° C. These polymers can exhibit a brittle fracture mechanism in which there is little or no plastic deformation prior to failure. As a result, a stent fabricated from such polymers can have insufficient toughness for the range of use of a stent.

One way to increase fracture toughness of a low fracture toughness polymer under physiological conditions is to blend it with another polymer having a higher or relatively high fracture toughness under physiological conditions, such that the higher fracture toughness polymer is also immiscible and forms a discrete phase from the low fracture toughness polymer. The discrete phase can absorb energy arising from stress imparted to a device made from the blend to increase the fracture toughness of the device. To ensure good energy transfer between interfaces of the phases, it is important that there be sufficient bonding or adhesion between the phases. See, Y. Wang, etc. Journal of Polymer Science Part A: Polymer Chemistry, 39, 2001, 2755-2766.

Certain embodiments of an implantable medical device can include a structural element that is made at least in part of a polymer blend/bioceramic composite. In an embodiment, the polymer blend can include a mixture of a matrix polymer with a modifier polymer, the matrix polymer being a majority of the polymer blend. The modifier polymer can be a block copolymer with the matrix polymer being immiscible with at least some of the blocks or segments of the modifier polymer. The polymer blend/bioceramic composite can also include a plurality of bioceramic particles dispersed within the polymer blend.

Since at least some of the blocks or segments of the modifier polymer are immiscible with the matrix polymer, the composite can include a continuous polymer phase and a discrete polymer phase within the continuous phase. The bioceramic particles can be dispersed within the continuous phase, the discrete phase, or both the discrete and continuous phases.

Furthermore, the continuous phase can include the matrix polymer and the discrete phase can include the immiscible blocks of the modifier polymer. In one embodiment, the matrix polymer has a relatively low fracture toughness at physiological conditions and the modifier polymer has a higher fracture toughness at physiological conditions. The modifier polymer or discrete phase tends to increase the toughness of the matrix polymer, and thus the composite.

In some embodiments, the modifier polymer can have discrete phase segments and anchor segments. The discrete phase segments are immiscible with the matrix polymer so that the discrete phase segments are in the discrete phase. The anchor segments are miscible with the matrix polymer so that the anchor segments at least partially phase separate from the discrete phase into the continuous phase.

Figure 1B:
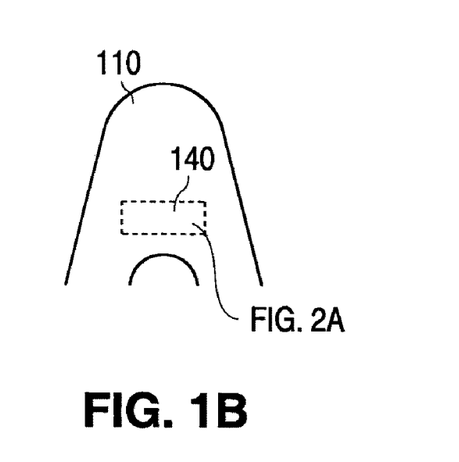
FIG. 1B depicts a section of a structural element from the stent depicted in FIG. 1A.
Figure 2:
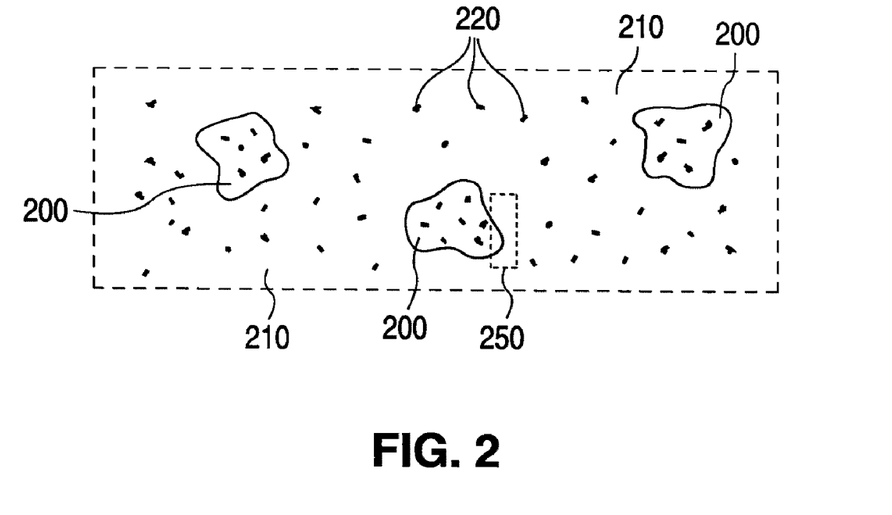
FIG. 2 depicts a schematic close-up view of the section depicted in FIG. 1B.

FIG. 1B depicts a section of a segment 110 of strut 105 from the stent depicted in FIG. 1A. FIG. 2 depicts a microscopic view of a portion 140 of segment 110 of the strut as depicted in FIG. 1B. Portion 140 includes a discrete phase 200 within a continuous phase 210. Bioceramic particles 220 are mixed or dispersed within discrete phase 200 and continuous phase 210.

Figure 3:
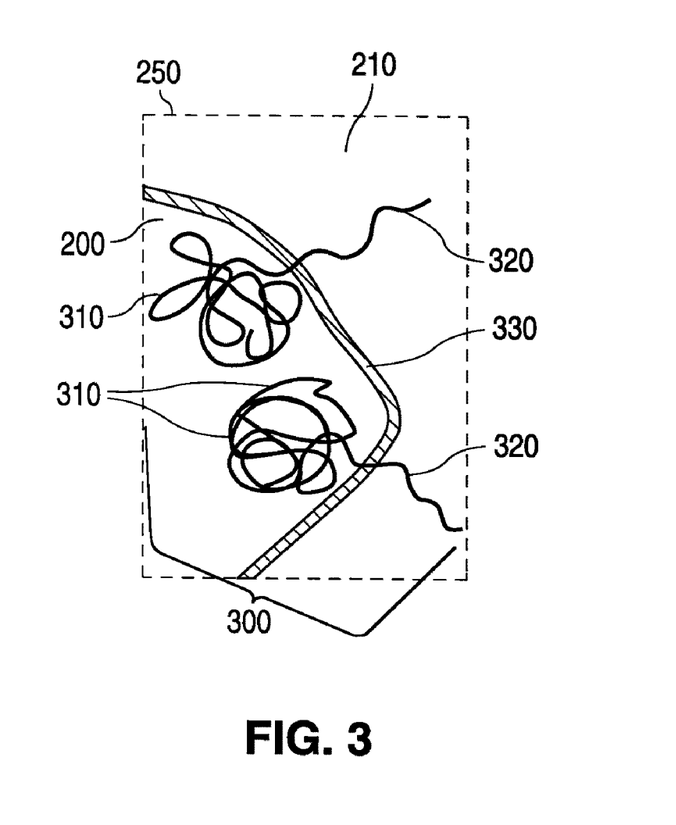
FIG. 3 depicts a schematic close-up view of an interface between a discrete polymer phase and a continuous polymer phase.

FIG. 3 depicts a schematic close-up view of section 250 including an interface between discrete phase 200 and continuous polymer phase 210. A modifier polymer 300 is shown to have discrete phase segments 310 and anchor segments 320. Line 330 is meant to delineate the boundary between discrete phase 200 and continuous phase 210. Anchor segments 320 are shown to be phase separated from discrete phase 200 into continuous phase 210.

It is believed that when a device is placed under stress, the discrete phase tends to absorb energy when a fracture starts to propagate through a structural element. Crack propagation through the continuous phase may then be reduced or inhibited. As a result, fracture toughness of the blend of the matrix polymer and the modifier polymer, and thus the structural element tends to be increased. Furthermore, the anchor segments tend to increase the adhesion between the discrete phase and the continuous phase. Thus, the anchor segments facilitate energy transfer between interfaces of the phases.

Furthermore, the toughness of the composite tends to be increased by the bioceramic particles dispersed within the blend. The bioceramic particles can increase the toughness and modulus of the polymer blend or composite. It is believed that bioceramic particles increase fracture toughness of the blend through dispersion of stress and strain in a device over a larger volume. The stress and strain can be divided into many small interactions involving numerous individual particles. For example, when a crack is initiated in the material and starts traveling through the polymer blend, the crack is dispersed or is broken up into finer and finer cracks due to interaction with the particles. Thus, the particles tend to dissipate the energy imparted to the device by the applied stress that caused the crack. In exemplary embodiments, a composite polymer blend can have at least 0.1 wt %, between 0.1 and 1 wt %, between 1 and 10 wt %, or between 10 and 20 wt % bioceramic particles.

In general, the increase in the toughness arising from the bioceramic particles is directly proportional to the size of the particles. For a give weight ratio of particles to matrix, as the size of the particles decreases the number of particles dispersed throughout the device per unit volume also increases. Thus, the number of particles to disperse the energy of applied stress to the device increases. Therefore, it is advantageous to use nanoparticles to increase the toughness of the polymer. It has been shown that the fracture toughness of a polymeric material can be improved by using nanoparticles as a discrete or reinforcing phase in a composite. J. of Applied Polymer Science, 94 (2004) 796-802.

In general, it is desirable for the bioceramic particles to be uniformly dispersed throughout the biodegradable polymer blend. The more uniform the dispersion of the particles results in more uniform properties of the composite and a device fabricated from the composite. For example, a uniform dispersion can result in a uniform increase in toughness and modulus and modification of degradation rate. In some embodiments, the bioceramic particles are uniformly or substantially uniformly dispersed within the biodegradable polymer blend.

In some embodiments, the discrete phase segments of the modifier polymer can include units or functional groups that are known to form polymers that have a higher fracture toughness than a matrix polymer such as PLLA. The discrete phase segments can form a discrete phase that is more flexible and has a lower modulus than the matrix polymer of the continuous phase. In one embodiment, the discrete phase segments of the modifier polymer can be a rubbery or elastomeric polymer. An "elastomer" or "rubbery" polymer refers to a polymer which can resist and recover from deformation produced by force, as in natural rubber. In one embodiment, elastomers or rubbery polymers can be stretched repeatedly to at least twice their original length and, immediately upon release of the stress, return with force to their approximate original length. In another embodiment, elastomers or rubbery polymers are substantially or completely amorphous polymers that are above their glass transition temperatures. In an embodiment, the discrete phase segments of the modifier polymer have a Tg below body temperature.

Biodegradable polymers having a relatively high fracture toughness include, but are not limited to, polycaprolactone (PCL) and poly(tetramethyl carbonate) (PTMC). PCL and PTMC are immiscible in PLLA. Thus, some embodiments of the discrete phase segments of the modifier polymer can include caprolactone (CL) and/or tetramethyl carbonate (TMC) monomers. The fraction of the CL and/or TMC monomers can be high enough that the discrete phase segments are immiscible in the PLLA.

Furthermore, a matrix polymer, such as PLLA, can have a degradation rate that is slower than desired for certain stent treatments. Thus, in additional embodiments the modifier polymer can include hydrolytically degradable units or functional groups that provide desired degradation characteristics. In some embodiment, the discrete phase segments of the modifier polymer can include functional groups or monomers that increase water penetration and content in the discrete phase and in the continuous phase. In particular, the discrete phase segments can include monomers that have a higher affinity for water and/or are more hydrolytically active than the matrix polymer. For example, the discrete phase segments can include glycolide (GA) monomers which are faster degrading than L-lactide monomers.

In other embodiments, the discrete phase segments can include units that increase the fracture toughness of the polymer blend and units that increase the degradation rate of the polymer blend. In an embodiment, the discrete phase segments can include both CL and GA monomers. In particular, the discrete phase segments can be poly(glycolide-co-c-caprolactone) (P(GA-co-CL)). P(GA-co-CL) discrete phase segments can have alternating or random GA and CL monomers. The faster degrading GA monomers can increase the degradation rate of the polymer blend by increasing the equilibrium water content and penetration into the structural element. The acidic and hydrophilic degradation products of the GA segments also act to increase the degradation rate of the polymer blend.

In some embodiments, the flexibility and degradation rate of the discrete phase segments can be adjusted by the ratio of fast degrading and toughness enhancing units. As the ratio of CL, for example, increases in P(GA-co-CL) segments, the polymer becomes more flexible and tougher. The Tg of the discrete phase segments can be tuned to a desired value by adjusting the ratio of component monomers. For example, the Tg of the discrete phase may be engineered to be less than a body temperature to provide a more flexible discrete phase under physiological conditions. Additionally, the degradation rate of the discrete phase segments, and thus the blend, can be increased by increasing the fraction of GA in the discrete phase segments. In exemplary embodiments, the P(GA-co-CL) segments can have greater than 1 wt %, 5 wt %, 20 wt %, 50 wt %, 70 wt %, 80 wt %, or 90 wt % GA monomer.

In one embodiment, the modifier polymer can include P(GA-co-CL)-b-PLLA or PLLA-b-P(GA-co-CL). In each case, the discrete phase segment is P(GA-co-CL) and the anchor segment is PLLA. In a binary polymer blend of a modifier polymer of P(GA-co-CL)-b-PLLA and/or PLLA-b-P(GA-co-CL) with a matrix polymer of PLLA, the PLLA anchor segment of the modifier polymer can phase separate into the PLLA matrix of the continuous phase. The PLLA anchor segment can bind the discrete phase with the continuous phase, facilitating the increase in the fracture toughness of the polymer blend.

In exemplary embodiments, the polymer blend/bioceramic composite can include about 1-30 wt % or 5-20 wt % of a modifier polymer and about 75-95 wt % of matrix polymer. The polymer blend/bioceramic composite can further include at least about 0.1 wt %, between 0.1 and 1 wt %, between 1 and 10%, or between 10 and 20 wt % bioceramic particles.

In further embodiments, the matrix polymer can be a copolymer. In some embodiments, a matrix copolymer can be composed of a primary functional group and at least one additional secondary functional group. The copolymer may be a random copolymer including the primary functional group and at least one additional secondary functional group. In an embodiment, the copolymer with at least one secondary functional group can have a higher degradation rate than a homopolymer composed of the primary functional group. A secondary functional group can have a greater affinity for water or be more hydrolytically active than the secondary functional group. In some exemplary embodiments, the weight percent of the secondary functional group in the copolymer can be at least about 1%, 5%, 10%, 15%, 30%, 40%, or, at least about 50%.

In an exemplary embodiment, the matrix copolymer can be poly(L-lactide-co-glycolide) (LPLG). The primary functional group can be L-lactide and the secondary functional group can be GA. The weight percent of the GA in the copolymer can be at least about 1%, 5%, 10%, 15%, 30%, 40%, or at least about 50%. In certain exemplary embodiments, the weight percent of the GA group can be adjusted so that the degradation time of a stent, with dispersed bioceramic particles, can be less than 18 months, 12 months, 8 months, 5 months, 3 months, or more narrowly, less than 3 month.

Additionally, the anchor segment of the modifier polymer can be selected so that the anchor segment is miscible with the matrix copolymer. In one embodiment, the anchor segment can have the same composition as the matrix copolymer. In another embodiment, the anchor segment can have a composition different from the matrix copolymer, but close enough so that the anchor segment is miscible with the matrix polymer. In another embodiment, the anchor segment can have composition different from the matrix polymer with the anchor segments being miscible with the matrix polymer.

Some embodiments can include a matrix polymer of PLLA and anchor blocks that include 100% L-lactide units or both L-lactide and GA units. Other embodiments can include a matrix polymer of LPLG and anchor blocks that include 100% L-lactide units or both L-lactide and GA units.

In some embodiments, a blend for fabricating an implantable medical device can be a ternary blend of the matrix polymer, a modifier polymer with discrete phase segments and an anchor block, and a discrete phase copolymer composed of discrete phase segments of the modifier polymer. The matrix polymer can form a continuous phase and the discrete phase copolymer can form a discrete phase within the continuous phase. The modifier polymer may act as a compatibilizer for the matrix polymer and the discrete phase copolymer by facilitating adhesion between the discrete and continuous phases. In one embodiment, the copolymer with discrete phase segments is a majority of the discrete phase.

In an exemplary embodiment, a ternary blend can include PLLA as the matrix polymer; P(GA-co-CL) copolymer; and P(GA-co-CL)-b-PLLA and/or PLLA-b-P(GA-co-CL) as the modifier polymer. In such embodiments, P(GA-co-CL) copolymer is in the discrete phase along with P(GA-co-CL) segments of the modifier polymer. PLLA of the modifier polymer phase separates into the PLLA continuous phase. In another exemplary embodiment, a ternary blend can include LGLG as the matrix polymer; P(GA-co-CL) copolymer; and P(GA-co-CL)-b-LPLG and/or LPLG-b-P(GA-co-CL) as the modifier polymer. In such embodiments, P(GA-co-CL) copolymer is in the discrete phase along with P(GA-co-CL) segments of the modifier polymer. LPLG of the modifier polymer phase separates into the LPLG continuous phase.

In exemplary embodiments, a ternary polymer blend for a polymer blend/bioceramic composite can include about 5-25 wt % of a discrete phase copolymer, about 0.5-2 wt % of a modifier polymer, and about 75-95 wt % of matrix polymer. The matrix polymer can be PLLA, the discrete phase copolymer can be P(GA-co-CL), and the modifier polymer can be PLLA-b-P(GA-co-CL) and/or PLLA-b-P(GA-co-CL). The polymer blend/bioceramic composite can include at least 0.1 wt %, between 0.1 and 1 wt %, between 1 and 10%, or between 10 and 20 wt % bioceramic particles.

Figure 4:
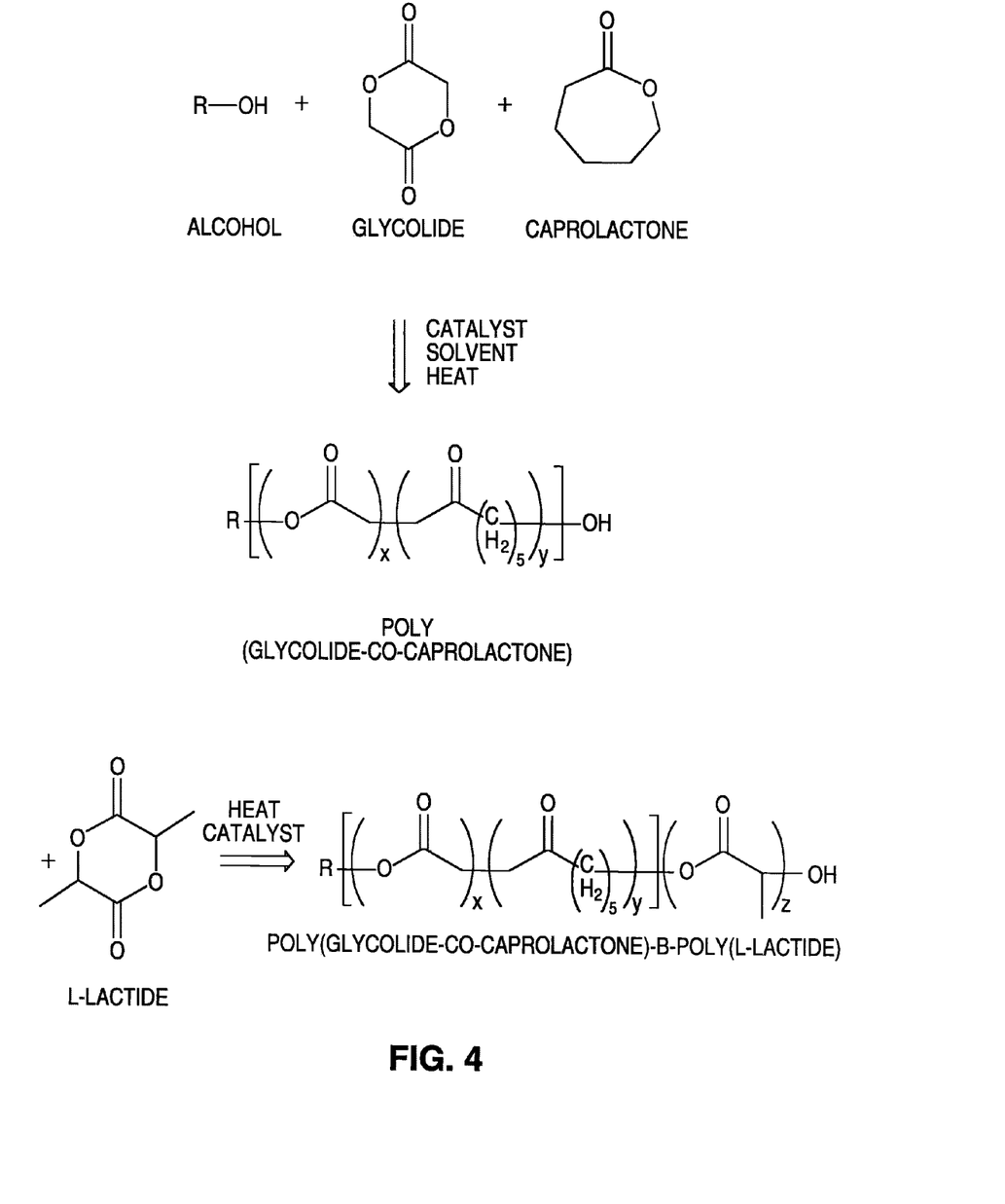
FIG. 4 depicts a synthesis scheme of a modifier polymer.
Figure 5A:
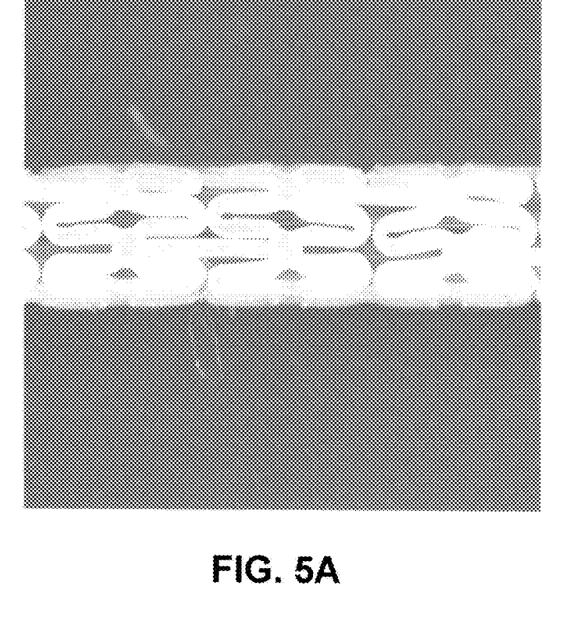
FIGS. 5A-D depict photographic images of the stent samples of crimper No. 1 before expansion, expanded to 3.0 mm, expanded to 3.5 mm, and after expansion to 4.0 mm, respectively.
Figure 5B:
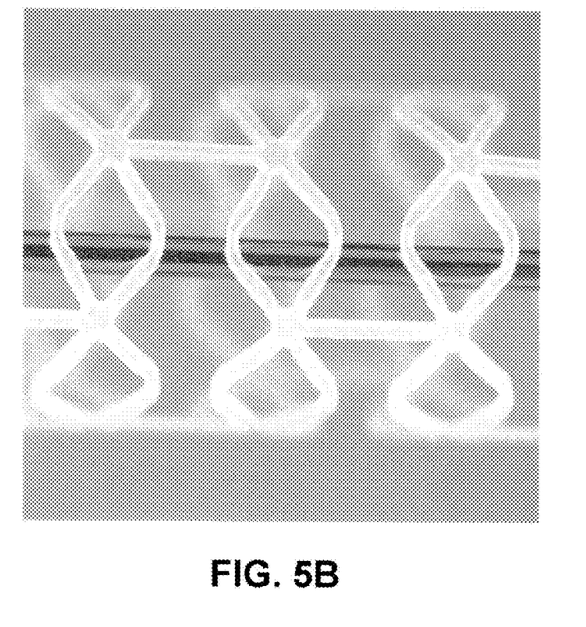
Figure 5C:
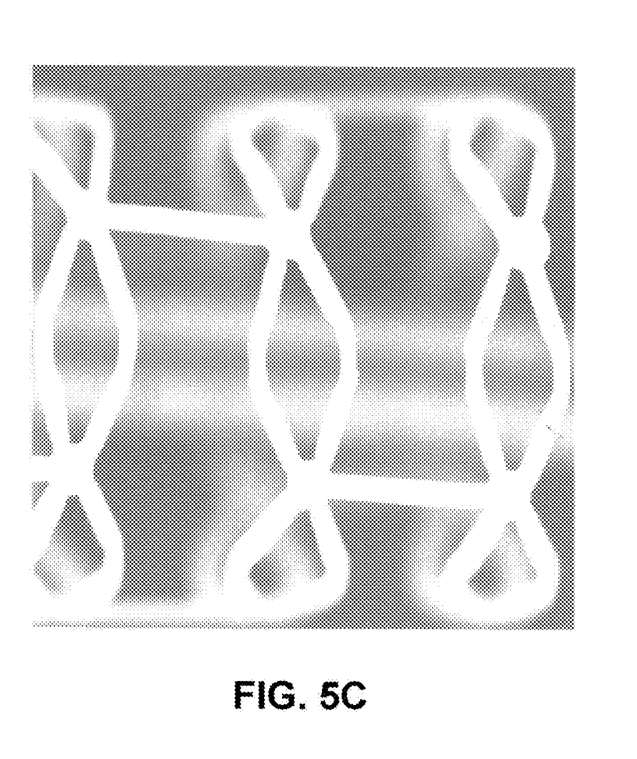
Figure 5D:
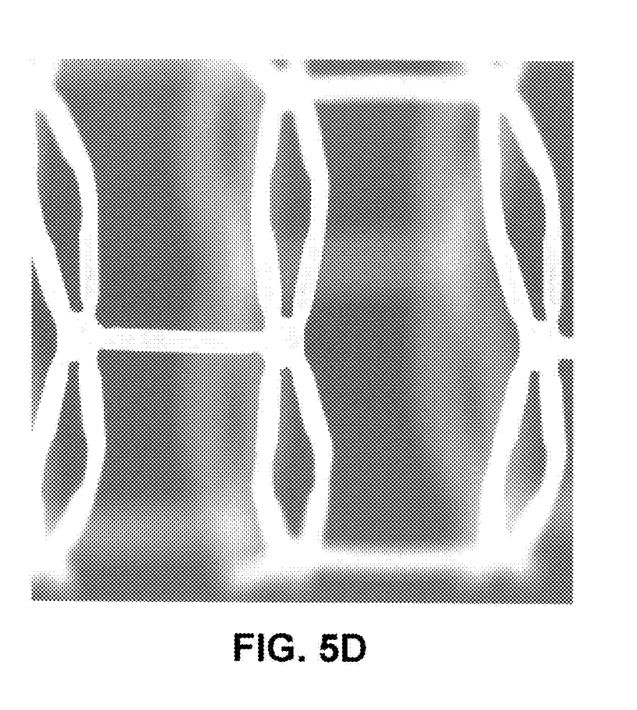
Figure 6A:
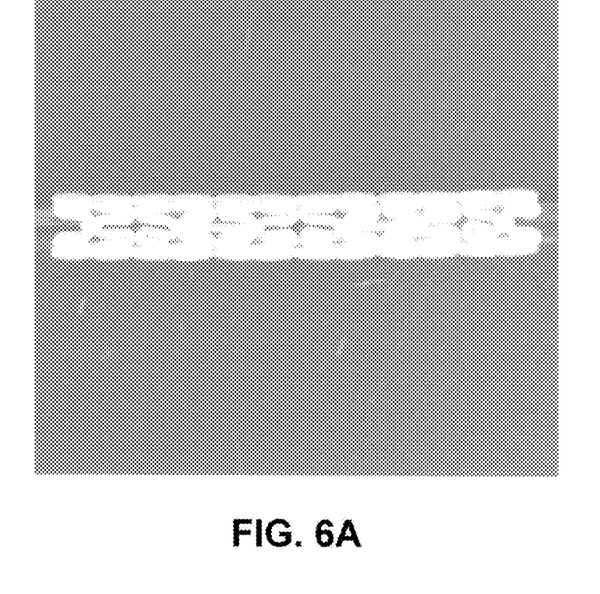
FIGS. 6A-D depict photographic images of the stent samples of crimper No. 1 before expansion, expanded to 3.0 mm, expanded to 3.5 mm, and after expansion to 4.0 mm, respectively.
Figure 6B:
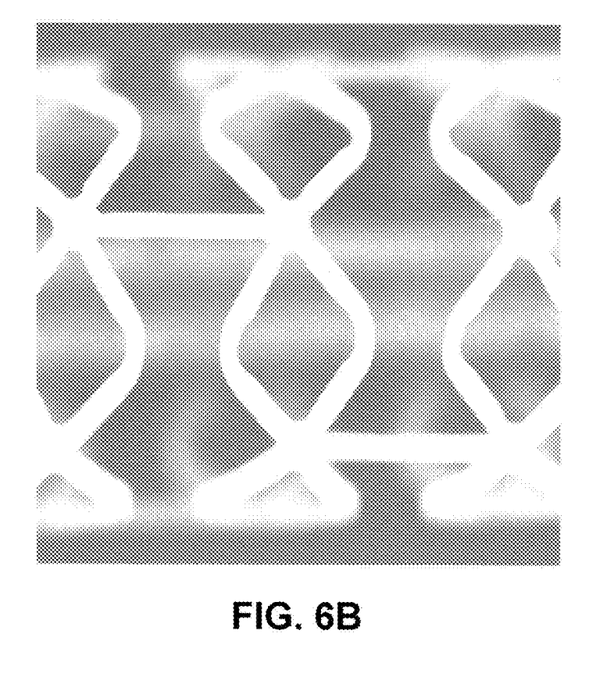
Figure 6C:
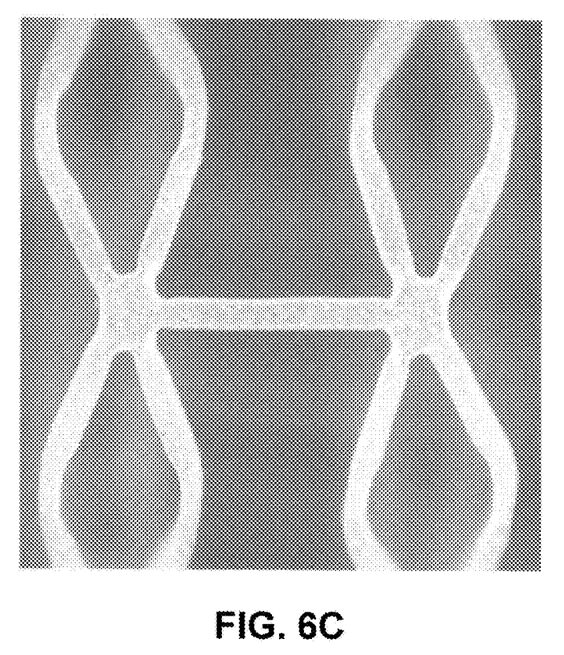
Figure 6D:
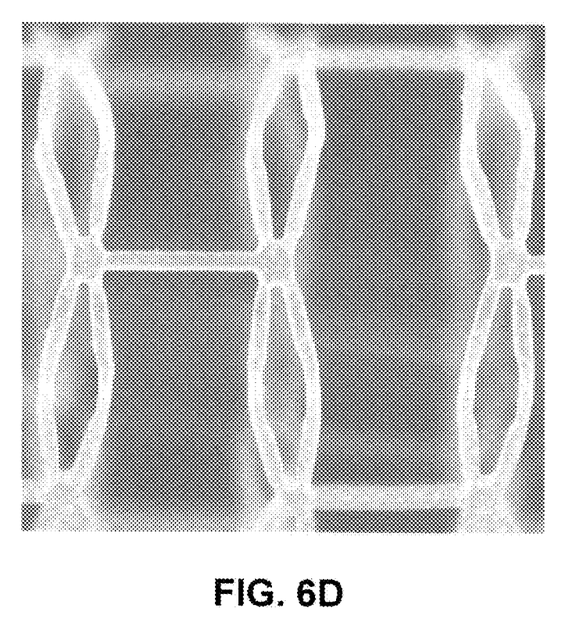

In some embodiments, a modifier polymer, such as P(GA-co-CL)-b-PLLA or P(GA-co-CL)-b-LPLG, can be formed by solution-based polymerization. Other methods used to form the modifier polymers are also possible, such as, without limitation, melt phase polymerization. In solution-based polymerization, all the reactive components involved in the polymerization reaction are dissolved in a solvent. To prepare P(GA-co-CL)-b-PLLA copolymer, P(GA-co-CL) may be prepared first by solution polymerization and then employed as a macro-initiator to initiate the polymerization of L-lactide monomers to form the PLLA segment, as illustrated in FIG. 4. Specifically, P(GA-co-CL) segments are formed first by mixing GA monomers and CL monomers with a solvent to form a solution. In the solution, the GA and CL monomers react to form P(GA-co-CL). L-lactide monomers can then be added to the solution or another solution containing the formed P(GA-co-CL). The L-lactide monomers react with P(GA-co-CL) to form P(GA-co-CL)-b-PLLA.

In one embodiment, the L-lactide monomers react in the same solution as the solution used to form P(GA-co-CL). Alternatively, the L-lactide monomers can react in a solution having a different solvent than the solution for forming P(GA-co-CL). The solvent(s) for forming the PLLA anchor segment can be selected so that the P(GA-co-CL) copolymer is soluble in the solvent(s) so that the copolymer can further copolymerize with L-lactide monomers.

In other embodiments, P(GA-co-CL)-b-PLLA can be formed by reacting P(GA-co-CL) copolymer swollen with a solvent with L-lactide monomers. One of skill in the art can select a solvent that swells but does not dissolve P(GA-co-CL). P(GA-co-CL) copolymer is swollen by a solvent after it is formed so that the P(GA-co-CL) copolymer can react with added L-lactide monomers.

In another embodiment, the synthesis of the PLLA-b-P(GA-co-CL) copolymer can be performed by first synthesizing the PLLA block. The L-lactide monomers can be mixed with a solvent to form a solution. GA monomers and CL monomers are added to a solution containing the PLLA that is formed to form PLLA-b-P(GA-co-CL) copolymer. The solution can be the same solution used to form the PLLA or a solution containing a different solvent.

In one embodiment, the solvent for use in synthesizing the copolymer is devoid of alcohol functional groups. Such alcoholic groups may act as initiators for chain growth in the polymer. Solvents used to synthesize the copolymer include, but are not limited to, chloroform, toluene, xylene, and cyclohexane. Initiators to facilitate the synthesis of the copolymer include, but are not limited to, dodecanol, ethanol, ethylene glycol, and polyethylene glycol. Catalysts used to facilitate the synthesis of the copolymer include, but are not limited to, stannous octoate and stannous trifluoromethane sulfonate.

In some embodiments, the polymer blend/bioceramic composite can be formed by melt blending. In melt blending the bioceramic particles are mixed with a polymer melt. The particles can be mixed with the polymer melt using extrusion or batch processing. A composite of the polymer blend and bioceramic particles can be extruded to form a polymer construct, such as a tube. A stent can then be fabricated from the tube.

In one embodiment, the bioceramic particles can be combined with a polymer blend in a powdered or granular form prior to melting of the polymer. The particles and polymer can be mixed using mechanical mixing or stirring such as agitation of the particles and polymer in a container or a mixer. The agitated mixture can then be heated to a temperature above the melt temperature of at least one of the polymers of the polymer blend in an extruder or using batch processing.

In further embodiments, a method of making a polymer blend/bioceramic composite for a medical device can include preparing the composite from a suspension of bioceramic particles and a polymer solution. A potential problem with the mechanical mixing or stirring techniques discussed above is that the polymer and particles may separate into regions or layers. This is particularly a problem with respect to smaller particles such as nanoparticles. Additionally, it may be difficult to obtain a uniform dispersion by mixing particles with a polymer melt since particles can agglomerate or form clusters. The mechanical mixing in an extruder or in batch processing may not be sufficient to break up the clusters, resulting in a nonuniform mixture of bioceramic particles and polymer blend. Bioceramic particles may be more uniformly dispersed in a composite formed from a suspension.

Certain embodiments of a method of forming an implantable medical device may include forming a polymer blend/bioceramic composite from a suspension including bioceramic particles suspended in a polymer solution. A "suspension" is a mixture in which particles are suspended or dispersed in a fluid. The polymer solution can include a polymer dissolved in a fluid that is a solvent for the polymer. The particles can be mixed with the fluid before or after dissolving the polymer in the fluid. Various mechanical mixing methods known to those of skill in the art may be used to disperse the bioceramic particles in the suspension. In one embodiment, dispersing the particles can be facilitated by an ultrasonic mixer.

The method may further include combining the suspension with a second fluid that is a poor solvent for the polymer. At least some of polymer may precipitate upon combining the suspension solution with the second fluid. In some embodiments, at least some of the bioceramic particles may precipitate from the suspension with the precipitated polymer to form a composite mixture of bioceramic particles and the polymer. The precipitated composite mixture may then be filtered out of the solvent. The filtered composite mixture can be dried to remove residual solvent. For example, the composite mixture can be dried in a vacuum oven or by blowing heated gas on the mixture.

The polymer solution can include, for example, a matrix polymer, modifier polymer, a polymer of discrete phase segments, or a combination thereof dissolved in a solvent. Exemplary polymers may include, but are not limited to, PLLA, PDLA, LPLG, P(GA-co-CL), PGA, PTMC, P(GA-co-CL)-b-PLLA, and PLLA-b-P(GA-co-CL). Representative solvents for such polymers can include toluene and chloroform. Representative poor solvents for these polymers that may be used to precipitate the polymer can include methanol, ethanol, isopropanol, and various alkanes such as hexane or heptane.

It is believed that in a suspension including bioceramic nanoparticles, the particles can have strong interactions with polymer chains in solution which can result in particles becoming encapsulated or surrounded by polymer chains. Thus, when the polymer is precipitated from the solution, the interactions of the particles with the polymer can overcome interactions of the particles with the solution so that the particles precipitate with the polymer.

Additionally, it has been observed that both the degree of precipitation of particles and the degree of dispersion of particles within the precipitated polymer depend upon the amount of polymer dissolved in the solution. The degree of precipitation refers to the amount of particles that precipitate out of the suspension. The degree of dispersion of particles within the precipitated polymer refers to the degree of mixing of the particles with the precipitated polymer.

The amount of polymer can be quantified by the weight percent of the polymer in the suspension solution. In addition, the viscosity of the solution is also related to the amount of polymer in the solution. The higher the weight percent of dissolved polymer, the higher is the viscosity of the suspension solution.

For a given concentration of suspended particles, as weight percent of dissolved polymer or viscosity is reduced, the degree of precipitation of particles is reduced. This is likely due to the reduced interaction of the particles with the polymer chains. Thus, at lower weight percent of polymer or viscosity, the amount of particles precipitating can be relatively low.

Additionally, for a given concentration of suspended particles, as the weight percent of polymer or viscosity of the solution is increased beyond an observed range, the degree of dispersion of particles in the precipitated polymer tends to decrease. It is believed that at higher weight percent of polymer or higher viscosity, the interactions between polymer chains reduce the interaction of particles with polymer chains that cause particles to precipitate. For example, particles may be unable to move freely among the polymer chains.

A given suspension has a particular combination of type of particles, particle concentration, and solvent. For this given suspension, the polymer weight percent or viscosity can be varied to obtain both a desired degree of precipitation of particles and degree of dispersion of particles in the precipitated polymer. Thus, there may be a range of polymer weight percent or viscosity that can result in a desired degree of precipitation of particles and degree of dispersion of particles in precipitated polymer.

Additionally, the manner of combining the suspension with the poor solvent can also affect the degree of precipitation and degree of dispersion. For example, depositing a fine mist of small droplets of suspension into a poor solvent can more readily result in a desired degree of precipitation and degree of dispersion. Thus, the manner of combining the suspension with the poor solvent can influence the range of polymer weight percent or viscosity that results in a desired degree of precipitation and degree of dispersion.

Further embodiments of the method include conveying the composite mixture into an extruder. The composite mixture may be extruded at a temperature above the melting temperature of the polymers in the composite mixture and less than the melting temperature of the bioceramic particles. In some embodiments, the dried composite mixture may be broken into small pieces by, for example, chopping or grinding. Extruding smaller pieces of the composite mixture may lead to a more uniform distribution of the nanoparticles during the extrusion process.

The extruded composite mixture may then be formed into a polymer construct, such as a tube or sheet which can be rolled or bonded to form a tube. A medical device may then be fabricated from the construct. For example, a stent can be fabricated from a tube by laser machining a pattern in to the tube. In another embodiment, a polymer construct may be formed from the composite mixture using an injection molding apparatus.

Preparation of a Desired Amount of Precipitated Composite Mixture May Require a Large amount of solvent and precipitant. Therefore, in some embodiments, it may be advantageous to melt blend precipitated composite mixture with an amount of polymer in an extruder or in a batch process. The polymer can be the same or a different polymer of the precipitated composite mixture. For example, a relatively small amount of precipitated composite mixture that has a weight percent of bioceramic particles higher than is desired can be prepared. The precipitated composite mixture may be melt blended with an amount of biodegradable polymer to form a composite mixture that has a desired weight percent of bioceramic particles.

In some embodiments, a composite for use in fabricating an implantable device can be formed by first forming a composite mixture of a matrix polymer and bioceramic particles. The composite mixture can be formed by precipitation of a matrix polymer from a suspension of bioceramic particles in a matrix polymer solution. The composite mixture can then be mixed with a modifier polymer, for example, by extrusion. In one embodiment, a batch of the precipitated matrix polymer/bioceramic composite mixture can be formed with a higher weight percent of bioceramic particles than a target weight percent for a device. The batch can then be mixed with a matrix polymer and modifier polymer to obtain a polymer blend/bioceramic composite with the target weight percent of bioceramic particles. For example, a 100:1 composite containing PLLA and modifier polymer can be prepared by first making a batch of PLLA/bioceramic composite with a 2:1 ratio of PLLA to bioceramic particles. The 2:1 composite can then be mixed with PLLA and modifier polymer to obtain a 100:1 PLLA-modifier polymer blend/bioceramic composite.

In other embodiments, a composite for use in fabricating an implantable device can be formed by first forming a composite mixture of a modifier polymer and bioceramic particles. The composite mixture can be formed by precipitation of a modifier polymer from a suspension of bioceramic particles in a modifier polymer solution. The composite mixture can then be mixed with a matrix polymer, for example, by extrusion. In one embodiment, a batch of the precipitated modifier polymer/bioceramic composite mixture can be formed with a higher weight percent of bioceramic particles than a target weight percent for a device. The batch can then be mixed with a matrix polymer and modifier polymer to obtain a polymer blend/bioceramic composite with the target weight percent of bioceramic particles. For example, a 100:1 composite containing PLLA and modifier polymer can be prepared by first making a batch of modifier polymer/bioceramic composite with a 2:1 ratio of modifier polymer to bioceramic particles. The 2:1 composite can then be mixed with PLLA and modifier polymer to obtain a 100:1 PLLA-modifier polymer blend/bioceramic composite.

In some embodiments, the polymer blend/bioceramic composite can include bioabsorbable bioceramic particles dispersed within the polymer blend. The bioabsorbable bioceramic particles can increase the degradation rate of the composite and the degradation time of a device. In an embodiment, the degradation time of a polymer blend/bioceramic composite device can be tuned and/or adjusted to a desired time frame. As bioceramic particles erode within the polymeric matrix, the porosity of the polymer blend increases. The increased porosity increases the diffusion rate of moisture through the polymer blend, and thus, the equilibrium moisture content of the polymer blend. As a result, the degradation rate of the polymer blend is increased. The porous structure also increases the transport of degradation products out of the matrix, which also increases the degradation rate of the polymer blend.

In certain embodiments, the degradation rate and degradation time of the device can be tuned or controlled through variables such as the type of bioceramic material and the size and shape of particles. In some embodiments, bioceramic materials can be selected to have a higher degradation rate than the polymer blend. The faster the degradation rate of the bioceramic material, the faster the porosity of the polymer blend increases which results in a larger increase in the degradation rate of the polymer blend. Additionally, the size of the particles influence the time for erosion of the particles. The smaller the particles, the faster the erosion of the particles because of the higher surface area per unit mass of particles.

For example, nanoparticles may have a relatively fast erosion rate compared to microparticles. Additionally, elongated particles, such as fibers, may tend to erode faster on a per unit mass basis due to the higher surface area per unit mass of the particle. Also, short fibers may tend to erode faster than longer fibers. Short fibers refer to long fibers than have been cut into short lengths. In some embodiments, the short fibers may be made by forming fibers as described above, and cutting them into short lengths. In one embodiment, a length of at least a portion of the short fibers is substantially smaller than a diameter of the formed tube. For example, in some embodiments, the short fibers may be less than 0.05 mm long. In other embodiments, the short fibers may be between 0.05 and 8 mm long, or more narrowly between 0.1 and 0.4 mm long or 0.3 and 0.4 mm long.

Furthermore, the size and distribution of pores created by erosion of bioceramic particles can also influence the degradation rate and time of the polymer blend. Smaller particles, such as nanoparticles, create a porous network that exposes a larger volume of the polymer blend to bodily fluid than larger particles, like microparticles. As a result the degradation rate and time of the matrix may be higher when nanoparticles are used rather than microparticles.

Through appropriate selection of the type of material for the particles and the size and shape of the particles, the particles and a composite device can be designed to have selected erosion rates and degradation time. For example, the particles can designed erode away in several minutes, hours, days, or a month upon exposure to bodily fluid.

As indicated above, many biodegradable polymers degrade by the mechanism of hydrolysis. The rate of the hydrolysis reaction tends to increase as the pH decreases. Since the degradation products of such polymers as polylactides are acidic, the degradation products have an autocatalytic effect. Therefore, the pH of the degradation products of the bioceramics can also affect the degradation rate of a device. Therefore, bioceramic particles with acidic degradation by-products may further increase the rate of degradation of a polymer blend.

For example, tricalcium phosphate releases acidic degradation products. Thus, some embodiments may include a composite including a bioceramic having acidic degradation products upon exposure to bodily fluids. The acidic degradation products can increase the degradation rate of the polymer which can decrease the degradation time of the device.

In other embodiments, a composite can have bioceramic particles that have basic degradation products. For example, hydroxyapatite releases basic degradation products. The basic degradation products of the bioceramic particles can reduce the autocatalytic effect of the polymer blend degradation by neutralizing the acidic degradation products of the polymer degradation. In some embodiments, the basic degradation products of the bioceramic particles can reduce the degradation rate of the polymer blend.

In some embodiments, bioceramic particles may include an adhesion promoter to improve the adhesion between the particles and the polymer blend. In one embodiment, an adhesion promoter can include a coupling agent. A coupling agent refers to a chemical substance capable of reacting with both the bioceramic particle and the polymer blend of the composite material. A coupling agent acts as an interface between the polymer and the bioceramic particle to form a chemical bridge between the two to enhance adhesion.

The adhesion promoter may include, but is not limited to, silane and non-silane coupling agents. For example, the adhesion promoter may include 3-aminopropyltrimethoxysilane, 3-aminopropyltriethoxysilane, aminopropylmethyldiethoxy silane, organotrialkoxysilanes, titanates, zirconates, and organic acid-chromium chloride coordination complexes. In particular, 3-aminopropyltrimethoxysilane has been shown to facilitate adhesion between poly(L-lactide) and bioglass. Biomaterials 25 (2004) 2489-2500.

In some embodiments, the surface of the bioceramic particles may be treated with an adhesion promoter prior to mixing with the polymer blend. In one embodiment, the bioceramic particles can be treated with a solution containing the adhesion promoter. Treating can include, but is not limited to, coating, dipping, or spraying the particles with an adhesion promoter or a solution including the adhesion promoter. The particles can also be treated with a gas containing the adhesion promoter. In one embodiment, treatment of the bioceramic particles includes mixing the adhesion promoter with solution of distilled water and a solvent such as ethanol and then adding bioceramic particles. The bioceramic particles can then be separated from the solution, for example, by a centrifuge, and the particles can be dried. The bioceramic particles may then used to form a polymer composite. In an alternative embodiment, the adhesion promoter can be added to the particles during formation of the composite. For example, the adhesion promoter can be mixed with a polymer blend/bioceramic mixture during extrusion.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly (caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. For the purposes of the present invention, the following terms and definitions apply:

Bioceramics can include any ceramic material that is compatible with the human body. More generally, bioceramic materials can include any type of compatible inorganic material or inorganic/organic hybrid material. Bioceramic materials can include, but are not limited to, alumina, zirconia, apatites, calcium phosphates, silica based glasses or glass ceramics, and pyrolytic carbons. Bioceramic materials can be bioabsorbable and/or active. A bioceramic is active if it actively takes part in physiological processes. A bioceramic material can also be "inert," meaning that the material does not absorb or degrade under physiological conditions of the human body and does not actively take part in physiological processes.

Illustrative examples of apatites and other calcium phosphates, include, but are not limited to hydroxyapatite ($Ca_{10}(PO_4)_6(OH)_2$), floroapatite ($Ca_{10}(PO_4)_6F_2$), carbonate apatide ($Ca_{10}(PO_4)_6CO_3$), tricalcium phosphate ($Ca_3(PO_4)_2$), octacalcium phosphate ($Ca_8H_2(PO_4)6\text{-}5H_2O$), octacalcium phosphate ($Ca_8H_2(PO_4)6\text{-}5H_2O$), calcium pyrophosphate ($Ca_2P_2O_7.2H_2O$), tetracalcium phosphate ($Ca_4P_2O_9$), and dicalcium phosphate dehydrate ($CaHPO_4.2H_2O$).

The term bioceramics can also include bioactive glasses that are bioactive glass ceramics composed of compounds such as $SiO_2$, $Na_2O$, $CaO$, and $P_2O_5$. For example, a commercially available bioactive glass, Bioglass®, is derived from certain compositions of $SiO_2$—$Na2O$—$K_2O$—$CaO$—$MgO$—$P_2O_5$ systems. Some commercially available bioactive glasses include, but are not limited to:

45S5: 46.1 mol % $SiO2$, 26.9 mol % $CaO$, 24.4 mol % $Na_2O$ and 2.5 mol % $P_2O_5$;

58S: 60 mol % $SiO2$, 36 mol % $CaO$, and 4 mol % $P_2O_5$; and

S70C30: 70 mol % $SiO2$, 30 mol % $CaO$.

Another commercially available glass ceramic is A/W.

As indicated above, an implantable medical device such as a stent can be medicated by incorporating an active agent in a coating over the device or within the substrate of the device. In some embodiments, the ions released from bioceramics can have an additive therapeutic and/or a synergistic therapeutic effect to the active agent. For example, ions can be used in conjunction with anti-proliferative and/or anti-inflammatory agents.

Bioceramic particles can be partially or completely made from a biodegradable, bioabsorbable, or biostable ceramic. Examples of bioabsorbable bioceramics include various types of bioglass materials, tetracalcium phosphate, amorphous calcium phosphate, alpha-tricalcium phosphate, and beta-tricalcium phosphate. Biostable bioceramics include alumina and zirconia.

Various sizes of the bioceramic particles may be used in the composite. For example, the bioceramic particles can include, but are not limited to, nanoparticles and/or micro particles. A nanoparticle refers to a particle with a characteristic length (e.g., diameter) in the range of about 1 nm to about 1,000 nm. A microparticle refers to a particle with a characteristic length in the range of greater than 1,000 nm and less than about 10 micrometers. Additionally, bioceramic particles can be of various shapes, including but not limited to, spheres and fibers.

Additionally, the particles size distribution can be important in modifying the properties of the polymer. Generally, a narrow size distribution is preferable.

The composite of a structural element of a device may have between 0.01% and 10% of bioceramic particles by weight, or more narrowly, between 0.5% and 2% bioceramic particles by weight as compared to the polymer matrix of the composite.

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

Stents were fabricated from a polymer blend/bioceramic composite. PLLA is the matrix polymer and P(GA-co-CL)-b-PLLA and/or PLLA-b-P(GA-co-CL) is the modifier polymer. Calcium sulfate nanoparticles are the bioceramic nanoparticles. Calcium sulfate nanoparticles, were pretreated by PEG-PPG-PEG surface modifier. PEG refers to polyethylene glycol and PPG refers to polypropylene glycol. The weight ratio of matrix polymer to modifier polymer to bioceramic particles was 100:10:1.

The composite was fabricated according to methods described herein. The stents were fabricated from tubes made from the composite and the tubes were radially expanded. The expanded tubes were laser cut to form stents.

Compression, recoil, or expansion testing were performed on stent samples. Two different in-house crimpers were used, referred to here as crimper No. 1 and crimper No. 2. The stents were tested at a zero time point, i.e., after fabrication without aging.

After laser cutting, each stent sample was crimped onto a catheter balloon, packaged in a foil pouch, and sterilized with e-beam radiation. The stent samples were then removed from the pouches for the compression, recoil, and expansion tests.

Prior to compression testing, a stent sample from a pouch was deployed to 3.0 mm and removed from the catheter assembly. Compression tests were performed with an Instron testing machine obtained from Instron in Canton, Mass. A stent sample was placed between two flat plates. The plates were adjusted so that the distance between the plates was the diameter of the stent in an uncompressed state. The plates were then adjusted to compress the stent by 10%, 15%, 25%, and 50% of the uncompressed plate distance. A resistance force, the amount force in units of Newtons/mm that was necessary to keep the stent at each compression distance, was measured. The resistance force corresponds to a measure of the radial strength (Rs). The modulus was also measured.

Table 1A provides the compression test results from crimper No. 1 samples. The Rs and modulus correspond to 50% compression. Table 1B provides the compression test results from crimper No. 2 samples.

TABLE 1A

Compression test results corresponding to crimper No. 1.

| Stent # | Rs (psi) | Modulus (psi) |
|---|---|---|
| 1 | 5.521 | 342.6 |
| 2 | 4.853 | 355.2 |
| 3 | 3.345 | 218.3 |
| 4 | 5.375 | 315.0 |
| 5 | 5.029 | 190.8 |
| Avg | 4.825 | 284.4 |
| Std dev | 0.869 | 74.944 |

TABLE 1B

Compression test results corresponding to crimper No. 2.

| Stent # | Rs (psi) | Modulus (psi) |
|---|---|---|
| 1 | 4.303 | 316.9 |
| 2 | 3.549 | 201.3 |
| 3 | 4.829 | 257.6 |
| 4 | 5.198 | 399.5 |
| 5 | 4.792 | 372.8 |
| Avg | 4.534 | 309.6 |
| Std dev | 0.636 | 81.490 |

For recoil testing, a crimped stent sample was removed from the foil pouch and deployed with a balloon pressure of 8 atm. The diameter of the deployed stent was measured. The balloon was deflated and the diameter was measured again. The percent recoil was calculated from:

% Recoil=(Inflated Diameter−Deflated Diameter)/Inflated Diameter×100%

The Inflated Diameter is the diameter of a deployed stent prior to deflating the balloon and the Deflated Diameter is the diameter of the recoiled stent after deflating the balloon. The deployment of the stent also results in an increase in length of the stent. The percent change in length was calculated from:

% Length change=(Crimped length−Deployed length)/Crimped length×100%

Table 2A provides the results of the recoil test for five stent samples at zero time point for crimper No. 1. Table 2B provides the results of the recoil test for five stent samples at zero time point for crimper No. 2. The % Total Recoil given is the average of the recoil calculated at each point along the length of the stent.

TABLE 2A

Recoil test results corresponding to crimper No. 1.

| Stent # | % Total Recoil | % Length Change |
|---|---|---|
| 1 | 0.7% | 2.0% |
| 2 | 1.5% | 1.7% |
| 3 | 1.3% | 1.9% |
| 4 | 1.4% | 1.2% |
| 5 | 0.6% | 1.1% |
| Avg | 1.1% | 1.6% |
| Std dev | 0.4% | 0.4% |

TABLE 2B

Recoil test results corresponding to crimper No. 2.

| Stent # | % Total Recoil | % Length Change |
|---|---|---|
| 1 | 1.9% | 1.9% |
| 2 | 2.2% | 2.7% |
| 3 | 1.4% | 2.1% |
| 4 | 2.5% | 1.1% |
| 5 | −0.7% | 1.8% |
| Avg | 1.5% | 1.9% |
| Std dev | 1.3% | 0.6% |

For expansion testing, a crimped stent sample was removed from the foil pouch and deployed to an outer diameter first to 3.0 mm, then 3.5 mm, and then 4.0 mm. The number of cracks in the stent samples were counted at each deployment diameter.

Table 3A provides the number of cracks observed in the stent samples at zero time point when deployed at diameters of 3.5 mm and 4 mm for crimper No 1. Table 3B provides the number of cracks observed in the stent samples at zero time point when deployed at diameters of 3.5 mm and 4 mm for crimper No 2. The columns refer to the size of the cracks: "Micro" refers to micro-sized cracks, "<25%" refers to cracks less than 25% of the strut width, "<50%" refers to cracks less than 50% of the strut width, and ">50%" refers to cracks greater than 50% of the strut width. "A" refers to the "v-shaped" region or bending region of struts and "B" refers to a spider region at the intersection of 5 struts. The regions can be seen in FIGS. 5A-D. No broken struts were observed at either 3.5 mm or 4.0 mm deployment diameters.

TABLE 3A

Number of cracks observed at 3.5 mm and 4 mm deployment for the stent samples corresponding to crimper No. 1.

| Stent # | Laser used | micro | <25% | <50% | >50% | Broken Struts |
|---|---|---|---|---|---|---|
| Deployed to 3.5 mm | | | | | | |
| 1 | Blue | 1 | | | | |
| 2 | Green | | | | | |
| 3 | Blue | 1 | | | | |
| 4 | Green | | | | | |
| 5 | Blue | | | | | |
| Deployed to 4.0 mm | | | | | | |
| 1 | Blue | 1 | | | | |
| 2 | Green | | | | | |
| 3 | Blue | 1 | | | | |
| 4 | Green | | | | | |
| 5 | Blue | | | | | |

TABLE 3B

Number of cracks observed at 3.5 mm and 4 mm deployment for the stent samples corresponding to crimper No. 2.

| Stent # | Laser used | micro | <25% | <50% | >50% | Broken Struts |
|---|---|---|---|---|---|---|
| Deployed to 3.5 mm | | | | | | |
| 1 | Blue | | | | | |
| 2 | Green | | | | | |
| 3 | Blue | 1 | | | | |
| 4 | Green | | | | | |
| 5 | Blue | 1 | | | | |
| Deployed to 4.0 mm | | | | | | |
| 1 | Blue | | | | | |
| 2 | Green | | | | | |
| 3 | Blue | 1 | | | | |
| 4 | Green | | | | | |
| 5 | Blue | 1 | | | | |

FIGS. 5A-D depict photographic images of the stent samples of crimper No. 1 before expansion, expanded to 3.0 mm, expanded to 3.5 mm, and after expansion to 4.0 mm, respectively. FIGS. 6A-D depict photographic images of the stent samples of crimper No. 1 before expansion, expanded to 3.0 mm, expanded to 3.5 mm, and after expansion to 4.0 mm, respectively.

The testing results corresponding to the two crimpers are summarized in Table 4. There is only a slight difference between the results of the two crimpers, indicating that the measured properties are independent of the crimper than is used.

TABLE 4

Summary of testing results.

| | Recoil Value | Radial strength | Modulus | Estimated # of Cracks |
|---|---|---|---|---|
| Sta. Clara | 1.10% | 4.825 | 284.4 | 4 |
| BVS C.E.R | 1.50% | 4.534 | 309.6 | 4 |

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating an implantable medical device comprising:
    forming a suspension solution including a fluid, a matrix polymer and bioceramic particles, wherein the polymer is dissolved in the fluid, and wherein the bioceramic particles are dispersed in the solution;
    allowing at least some of matrix polymer to precipitate upon combining the suspension solution with a second fluid, the second fluid being a poor solvent for the matrix polymer, wherein at least some of the bioceramic particles precipitate with the precipitated polymer to form a composite mixture;
    mixing the composite mixture with a modifier polymer and additional matrix polymer to form a second composite mixture, the bioceramic particles being dispersed within the second composite mixture by the mixing, wherein the modifier polymer has discrete phase segments, the discrete phase segments being immiscible with the matrix polymer, the modifier polymer further comprising anchor segments that are miscible with the matrix polymer; and
    fabricating a medical device from the second composite mixture.

2. The method of claim 1, wherein the medical device is a stent.

3. The method of claim 1, wherein the matrix polymer is selected from the group consisting of poly(L-lactide), poly(L-lactide-co-glycolide), and a combination thereof.

4. The method of claim 1, wherein the discrete phase segments comprise monomers selected from the group consisting of caprolactone, trimethylene carbonate, and glycolide.

5. The method of claim 1, wherein the anchor segments are selected from the group consisting of poly(L-lactide), poly(L-lactide-co-glycolide), and a combination thereof.

6. The method of claim 1, wherein the modifier polymer is selected from the group consisting of poly(glycolide-co-ϵ-caprolactone)-b-poly(L-lactide), poly(L-lactide)-b-poly(glycolide-co-ϵ-caprolactone), poly(glycolide-co-c-caprolactone)-b-poly(L-lactide-co-glycolide), poly(L-lactide-co-glycolide)-b-poly(glycolide-co-ϵ-caprolactone), and a combination thereof.

7. The method of claim 1, wherein fabricating the medical device from the second composite mixture comprises forming a tube from the second composite mixture and cutting a stent pattern in the tube.

8. A method for fabricating an implantable medical device comprising:
    forming a suspension solution including a fluid, a modifier polymer and bioceramic particles, wherein the polymer is dissolved in the fluid, and wherein the bioceramic particles are dispersed in the solution;

allowing at least some of modifier polymer to precipitate upon combining the suspension solution with a second fluid, the second fluid being a poor solvent for the modifier polymer, wherein at least some of the bioceramic particles precipitate with the precipitated polymer to form a composite mixture;

mixing the composite mixture with the modifier polymer and a matrix polymer to form a second composite mixture, the bioceramic particles being dispersed within the second composite mixture by the mixing, wherein the modifier polymer has discrete phase segments, the discrete phase segments being immiscible with the matrix polymer, the modifier polymer further comprising anchor segments that are miscible with the matrix polymer; and fabricating a medical device from the second composite mixture.

9. The method of claim 8, wherein the medical device is a stent.

10. The method of claim 8, wherein the matrix polymer is selected from the group consisting of poly(L-lactide), poly (L-lactide-co-glycolide), and a combination thereof.

11. The method of claim 8, wherein the discrete phase segments comprise monomers selected from the group consisting of caprolactone, trimethylene carbonate, and glycolide.

12. The method of claim 8, wherein the anchor segments are selected from the group consisting of poly(L-lactide), poly(L-lactide-co-glycolide), and a combination thereof.

13. The method of claim 8, wherein the modifier polymer is selected from the group consisting of poly(glycolide-co-$\epsilon$-caprolactone)-b-poly(L-lactide), poly(L-lactide)-b-poly(glycolide-co-c-caprolactone), poly(glycolide-co-$\epsilon$-caprolactone)-b-poly(L-lactide-co-glycolide), poly(L-lactide-co-glycolide)-b-poly(glycolide-co-$\epsilon$-caprolactone), and a combination thereof.

14. The method of claim 8, wherein fabricating the medical device from the second composite mixture comprises forming a tube from the second composite mixture and cutting a stent pattern in the tube.

* * * * *